US008163154B1

(12) United States Patent
Hatch et al.

(10) Patent No.: US 8,163,154 B1
(45) Date of Patent: Apr. 24, 2012

(54) METHOD FOR VOLTAGE-GATED PROTEIN FRACTIONATION

(75) Inventors: Anson Hatch, Tracy, CA (US); Anup K. Singh, Danville, CA (US)

(73) Assignee: Sandia Corporation, Albuquerque, NM (US)

( * ) Notice: Subject to any disclaimer, the term of this patent is extended or adjusted under 35 U.S.C. 154(b) by 1075 days.

(21) Appl. No.: 11/779,407

(22) Filed: Jul. 18, 2007

Related U.S. Application Data (63) Continuation-in-part of application No. 11/536,753, filed on Sep. 29, 2006, now Pat. No. 7,828,948.

(60) Provisional application No. 60/875,743, filed on Dec. 18, 2006.

(51) Int. Cl.
*B01D 61/58* (2006.01)
(52) U.S. Cl. .................. 204/543; 204/518; 204/451
(58) Field of Classification Search .................. 204/450, 204/451, 453, 518, 543, 551
See application file for complete search history.

(56) References Cited

U.S. PATENT DOCUMENTS

| | | | |
|---|---|---|---|
| 6,391,937 | B1 | 5/2002 | Beuhler |
| 6,673,615 | B2 | 1/2004 | Denison |
| 7,005,264 | B2 | 2/2006 | Su |
| 7,114,378 | B1 | 10/2006 | Barth |
| 2002/0146839 | A1 | 10/2002 | Guttman |
| 2005/0034990 | A1 | 2/2005 | Crooks |
| 2006/0180469 | A1 | 8/2006 | Han |
| 2006/0228717 | A1 | 10/2006 | Joyce |

OTHER PUBLICATIONS

Martin M. Chui; Ronald J. Phillips; Michael J. McCarthy; "Measurement of the Porous Microstructure of Hydrogels by Nuclear Magnetic Resonance", Journal of Colloid and Interface Science, 1995, vol. 174, pp. 336-344.
Debora Foguel; Gregorio Weber; "Pressure-induced Dissociation and Denaturation of Allophycocyanin at Subzero Temperatures", Journal of Biological Chemistry, 1995, vol. 270, No. 48, pp. 28759-28766.
Ellika U. Weber-Ban; Brian G. Reid; Andrew D. Miranker; Arthur L. Horwich; "Global unfolding of a substrate protein by the Hsp100 chaperone ClpA", Nature, 1999, vol. 401, pp. 90-93.
J. Han; H. G. Craighead; "Separation of Long DNA Molecules in a Microfabricated Entropic Trap Array", Science, 2000, vol. 288, No. 5468, pp. 1026-1029.
Shihai Huang; Kevin S. Ratliff; Andreas Matouschek; "Protein unfolding by the mitochondrial membrane potential," Nature Structural Biology, 2002, vol. 9, No. 4, pp. 301-307.
Jonathan J. Nakane; Mark Akeson; Andre Marziali; "Nanopore sensors for nucleic acid analysis", Journal of Physics: Condensed Matter, 2003, vol. 15, pp. 1365-1393.

(Continued)

*Primary Examiner* — J. Christopher Ball
(74) *Attorney, Agent, or Firm* — Timothy P. Evans (57) ABSTRACT

We report unique findings on the voltage dependence of protein exclusion from the pores of nanoporous polymer exclusion membranes. The pores are small enough that proteins are excluded from passage with low applied electric fields, but increasing the field enables proteins to pass through. The requisite field necessary for a change in exclusion is protein-specific with a correlation to protein size. The field-dependence of exclusion is important to consider for preconcentration applications. The ability to selectively gate proteins at exclusion membranes is also a promising means for manipulating and characterizing proteins. We show that field-gated exclusion can be used to selectively remove proteins from a mixture, or to selectively trap protein at one exclusion membrane in a series.

23 Claims, 7 Drawing Sheets

OTHER PUBLICATIONS

Jiali Li; Marc Gershow; Derek Stein; Eric Brandin; J. A. Golovchenko; "DNA molecules and configurations in a solid-state nanopore microscope", Nature Materials, 2003, vol. 2, pp. 611-615.

Nicholas C. Fitzkee; George D. Rose; "Reassessing random-coil statistics in unfolded proteins", Proceedings of the National Academy of Sciences, 2004, vol. 101, No. 34, pp. 12497-12502.

Sen Zhang; Eshwar Udho; Zhengyan Wu; R. John Collier; Alan Finkelstein; "Protein Translocation through Anthrax Toxin Channels Formed in Planar Lipid Bilayers", Biophysycal Journal, 2004, vol. 87, pp. 3842-3849.

Nathaniel Schaefle; Robert Sharp; "NMR Paramagnetic Relaxation of the Spin 2 Complex MnIIITSPP: A Unique Mechanism", Journal of Physical Chemistry, 2005, vol. 109, No. 15, pp. 3267-3275.

Lei Huang; Serdal Kirmizialtin; Dmitrii E. Makarov; "Computer simulations of the translocation and unfolding of a protein pulled mechanically through a pore", Journal of Chemical Physics, 2005, vol. 123, pp. 124903-1 to 124903-7.

Daniel Fologea; Marc Gershow; Bradley Ledden; David S. McNabb; Jene A. Golovchenko; Jiali Li; "Detecting Single Stranded DNA with a Solid State Nanopore", American Chemical Society, 2005, vol. 5, No. 10, pp. 1905-1909.

Alexander J. Wilcox; Jason Choy; Carlos Bustamante; Andreas Matouschek; "Effect of protein structure on mitochrondrial import", Proceedings of the National Academy of Sciences, 2005, vol. 102, No. 43, pp. 15435-15440.

Takehiro Sato; Masatoshi Esaki; Julio M. Fernandez; Toshiya Endo; "Comparison of the protein-unfolding pathways between mitochondrial protein import and atomic-force microscopy measurements", Proceedings of the National Academy of Sciences, 2005, vol. 102, No. 50, pp. 17999-18004.

T. Sakaue; "DNA electrophoresis in designed channels", The European Physical Journal E, 2006, vol. 19, pp. 477-487.

Anpan Han; Gregor Schurmann; Giampetro Mondin; Roland Andreas Bitterli; Nicole G. Hegelbach; Nico F. de Rooij; Urs Staufer; "Sensing protein molecules using nanofabricated pores", Applied Physics Letters, 2006, No. 88, pp. 093901-1 to 093901-3.

Serdal Kirmizialtin; Lei Huang; Dmitrii E. Makarov; "Computer simulations of protein translocation", Physica Status Solidii, 2006, vol. 243, No. 9, pp. 2038-2047.

Daniel K. West; David J. Brockwell; Emanuele Paci; "Prediction of the Translocation Kinetics of a Protein from Its Mechanical Properties", Biophysical Journal: Biophysical Letters, 2006, DOI: 10.1529, pp. L51-L53.

J. T. Mannion; C. H. Reccius; J. D. Cross; H. G. Craighead; "Conformational Analysis of Single DNA Molecules Undergoing Entropically Induced Motion in Nanochannels", Biophysical Journal, 2006, vol. 90, pp. 4538-4545.

Hendrik Dietz; Felix Berkemeier; Morten Bertz; Matthias Rief; "Anisotropic deformation response of single protein molecules", Proceedings of the National Academy of Sciences, 2006, vol. 103, No. 34, pp. 12724-12728.

Anson V. Hatch; Amy E. Herr; Daniel J. Throckmorton; James S. Brennan; Anup K. Singh; "Integrated Preconcentration SDS-PAGE of Proteins in Microchips Using Photopatterned Cross-Linked Polyacrylamide Gels", Analytical Chemistry, 2006, vol. 78, No. 14, pp. 4976-4984.

Martin Krayl; Joo Hyun Lim; Falk Martin; Bernard Guiard; Wolfgang Voos; "A Cooperative Action of the ATP-Dependent Import Motor Complex and the Inner Membrane Potential Drives Mitochondrial Preprotein Import", Molecular and Cellular Biology, 2007, vol. 27, No. 2, pp. 411-425.

METHOD FOR VOLTAGE-GATED PROTEIN FRACTIONATION

CROSS REFERENCE TO RELATED APPLICATIONS

This application is a continuation-in-part application of prior U.S. patent application Ser. No. 11/536,753 originally filed Sep. 29, 2006 now U.S. Pat. No. 7,828,948 entitled "PRECONCENTRATION AND SEPARATION OF ANALYTES IN MICROCHANNELS," and which are herein incorporated by reference in their entirety. The application further claims the benefit of provisional U.S. Patent Application Ser. No. 60/875,743 originally filed Dec. 18, 2006 entitled "APPARATUS AND METHOD FOR VOLTAGE-GATED PROTEIN TRANSPORT THROUGH NANOPOROUS MEMBRANES" from which benefit is claimed.

STATEMENT OF GOVERNMENT SUPPORT

The United States Government has a paid-up license in this invention and the right in limited circumstances to require the patent owner to license others on reasonable terms as provided for by the terms of contract No. DE-AC04-94AL85000 awarded by the U.S. Department of Energy to Sandia Corporation.

BACKGROUND OF THE INVENTION

Field of the Invention

The present invention relates generally to the field of microfluidics-based analysis and, more particularly, to a method for a size exclusion mechanism to selectively pass and therefore concentrate molecules such as proteins within a specific size range where only electrophoretic forces and physical barriers apply.

Differentiating piecewise transport of biomolecules such as DNA and proteins through nanopores appears to be a promising technique for characterizing, counting, and sequencing these species. Nanoporous size-exclusion membranes fabricated in microfluidic channels have been shown to be useful for concentrating proteins having molecular weights of greater than about 10 kDa by over 1,000-fold to improve on-chip assay sensitivities. We have found that by varying the strength of an applied electrical field it is possible to move proteins of varying size through these nanoporous membranes and thereby selectively fractionate them based on various physical and chemical parameters such as molecular weight, charge, crosslinking, and the like.

The translocation of proteins through nanopores, a vital cellular process, is the mechanism of entry for many protein toxins. Rather than shuttling bulky folded proteins through pores, systems have evolved to thread them as linear peptide strands through small pores (translocons) ~2 nm in diameter. Pores of this size will accommodate alpha-helical secondary structural elements but not folded domains. Protein translocation is generally assisted by chaperone proteins, but there is also speculation that transmembrane electrical potential helps drive protein unfolding and translocation. We find, however, that proteins can be driven by an electric field through pores of similar size in synthetic polymer membranes. Furthermore, protein translocation is switchable based on the applied electric field strength and properties of the protein, namely size, charge and quaternary structure. Above a protein-specific electric field threshold, proteins are driven through membrane pores, but below the threshold, proteins are excluded from the pores and can be enriched at the membrane face as is described in co-pending, commonly-owned U.S. patent application Ser. No. 11/536,753, herein incorporated by reference. This phenomenon can be exploited in lab-on-a-chip devices to selectively fractionate and preconcentrate proteins with single membranes or integrated membrane networks.

Passage of proteins through the pores at higher field strengths is attributed to partial unfolding or deformation of proteins due to the driving force of the applied field. The field-dependent exclusion mechanism could be useful as a multifaceted fractionation tool with single membranes or a network of membranes. Applications include step-wise voltage-tunable fractionation of a complex protein mixture in a simple chip with just one membrane.

SUMMARY

The present invention provides a method for fractionating or characterizing proteins based on their voltage-dependent electro-migration through nanopores of a polymer membrane. The nanoporous membranes were fabricated in situ in microchannels on a microchip using a photo-polymerization process. The pores are small enough (1-10 nm) that proteins are excluded from passage at low applied electric fields, but increasing the field enables proteins to pass through. The protein electro-migration process, therefore, has been found to be switchable based on the applied electric field strength and properties of the protein, particularly size, charge and quaternary structure.

The present invention also provides a device for fractionating proteins based on their voltage-dependent electro-migration through nanopores of a synthetic polymer membrane.

In some embodiments, the present invention provides a system which includes a network of microfluidic channels at least one of which comprises at least one in situ polymerized polymer membrane for initially preventing proteins suspended in a fluid from passing beyond a certain point within the microchannel.

The system may also provide a means for applying and maintaining a high voltage potential across at least one polymer membrane.

The microchannel network may also comprise additional size-excluding polymeric membranes, together with additional high voltage means across each membrane in order to provide for successively fractionating the protein suspension.

In most embodiments, the protein fractionation device will also include one or more side-branching microchannels disposed between successive size-excluding membranes to provide means for analyzing the protein fraction remaining between membranes following fractionation.

The size-excluding membranes may be prepared in an identical manner and therefore comprise pores that are within the same size range. Any one membrane also may be prepared with different concentrations or types of monomers and crosslinkers and therefore comprise pores that are within a different, preselected, size range.

In some embodiments, a processing area is provided for and may comprise one of the side-branching microfluidic channels. In some embodiments, the assay area comprises a porous polymeric membrane, a liquid sieving gel, or the like.

In some embodiments, the microfluidic channel further comprises electrodes attached thereto to provide a mobilization field such as an electric field.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIG. 3C illustrates that the exclusion threshold, $E_{50}$, correlates well with protein size at buffer conditions where the charge-to-mass ratio of the proteins is similar.

DETAILED DESCRIPTION OF EMBODIMENTS OF THE INVENTION

Figure 1A:
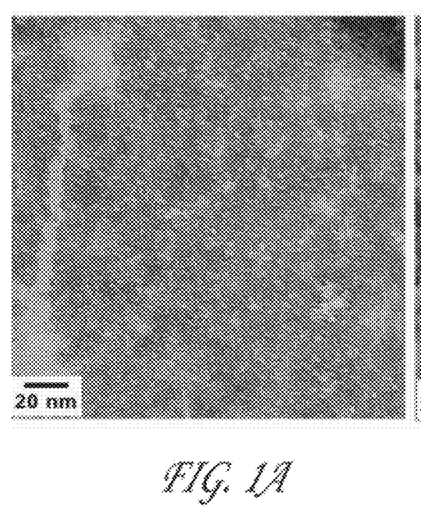
FIG. 1A shows a transmission electron microscope image of a bulk photopolymerized cross-linked polyacrylamide gel used in these studies (left, 22% T 6% C) having an average pore diameters of about 2 nm.
Figure 1B:
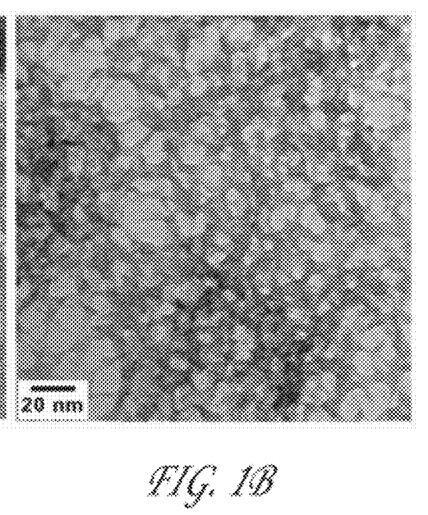
FIG. 1B shows a transmission electron microscope image of a bulk photopolymerized cross-linked polyacrylamide gel having a lower percentage gel (9% T 9% C) and having larger pore sizes (average pore diameter about 8.6 nm) more typical for sieving.

In order to demonstrate the present method, nanoporous membranes were incorporated at strategic points in various microchannels formed in fused silica chips obtained from Caliper Life Sciences, (Mountain View, Calif.). The membranes used herein comprised cross-linked polyacrylamide gels which were photo-polymerized in situ using methods previously described in commonly owned U.S. patent application Ser. Nos. 10/443,491 filed May 22, 2003, 10/646,808 filed Aug. 25, 2003, and 11/137,744 and 11/137,745 both filed May 24, 2005 herein incorporated by reference in their entirety and in U.S. Pat. No. 6,391,937, issued May 21, 2002, also incorporated by reference in its entirety. The size-exclusion membranes used herein for protein fractionation were prepared with a smaller average pore size then membranes generally used for capillary gel electrophoretic (CGE) sieving. FIG. 1A shows a photomicrograph taken by transmission electron microscopy (TEM) of a cross section of a polyacrylamide size-exclusion membrane having an average pore size of about 2 nm in diameter. A similar TEM photomicrograph taken of the pore structure of a typical sieving membrane is shown in FIG. 1B for comparison. This latter photograph shows an average pore size of about 8.6 nm in diameter.

To prepare the fused silica glass chip for exclusion membrane attachment the interior channels surfaces of the glass chip were first treated with a bi-functional reactive silane material, such as 3-(trimethoxysilyl)propyl methacrylate, (Sigma Chemical Company, St. Louis, Mo.). The silyl head group of this material covalently bonds to the exposed silica channel surfaces of the glass chip while the acrylate tail group extends outward to provide a functionalizing moiety to which the polymer exclusion membrane of the current embodiment attaches itself during photo-polymerization.

Figure 1C:
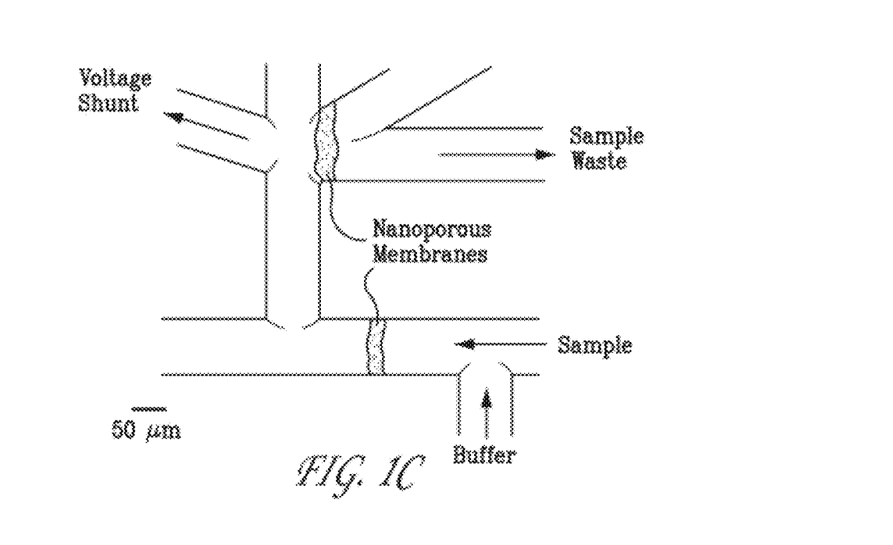
FIG. 1C shows a photomicrograph of a photo-polymerized nanoporous membrane in a glass microchannel.

An example of exclusion membranes placed in two microchannels on a glass chip is shown in FIG. 1C. The dimensions of these membranes typically measured about 15 μm to 100 μm in length as defined by a shaped beam UV laser. Exclusion membranes used in the current embodiment were about 30 μm deep by about 80 μm wide as defined by the etched geometry of the microfluidic chip.

Two types of nanoporous exclusion membranes were prepared utilizing different materials, but having similar pore sizes, and then tested for their ability to function as selective exclusion membranes. The first membrane type was prepared from cross-linked polyacrylamide (22% T, 6% C) such as described by Hatch, et al., ("Integrated preconcentration SDS-PAGE of proteins in microchips using photo-patterned cross-linked polyacrylamide gels," *Analytical Chemistry*, v. 78, 2006: pp. 4976-4984, herein incorporated by reference). The second membrane type was cross-linked zwitterionic methacrylate described by Song, et al., ("Electrophoretic Concentration of Proteins at Laser-Patterned Nanoporous Membranes in Microchips," *Analytical Chemistry*, v. 76, 2004: pp. 4589-4592, herein incorporated by reference). The average pore diameter of the former was estimated to be about 2 nm based on TEM imaging (see FIG. 1A) and in agreement with other analysis techniques for the range of acrylamide used. The pore diameters of the methacrylate membrane are estimated to be of similar size. Both types of these membranes have been to shown previously to concentrate proteins up to several orders of magnitude (op. cit., Hatch, et al. *Analytical Chemistry*, v. 78, 2006).

In addition to the size exclusion membrane, at least one cross-linked polyacrylamide sieving gel (8% T, 2.6% C) was introduced and photopolymerized in a side-separation channel disposed immediately adjacent to the size-exclusion membranes in order to provide for electrophoretic separation analysis of excluded protein fractions. After protein concentration and subsequent selective fractionation, excluded proteins were redirected from the exclusion membrane interface as a narrow band into the side-separation channel for protein sizing and/or immunoassay.

Figure 2A:
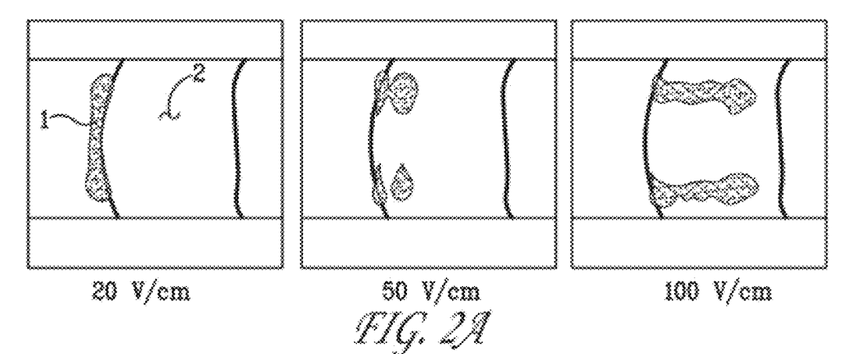
FIG. 2A shows fluorescently labeled BSA excluded in a narrow band from a zwitterionic membrane with an applied electric field, E, equal to 20V/cm while at high applied electric field potentials the fluorescently labeled BSA is driven into the membrane.
Figure 2B:
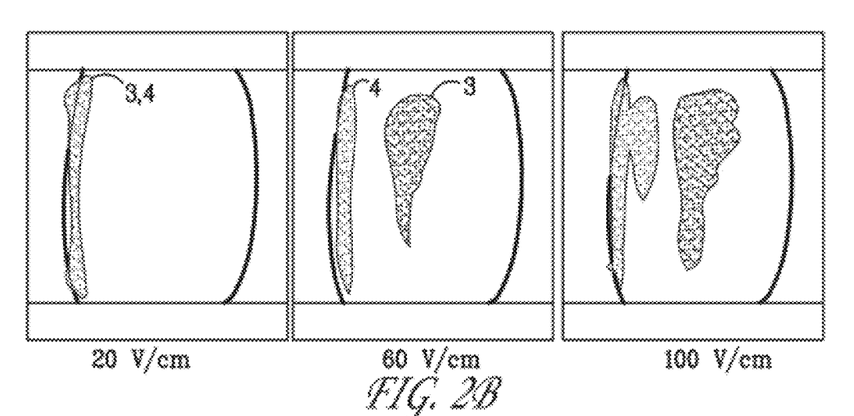
FIG. 2B shows fluorescently labeled BSA and ovalbumin are excluded from an acrylamide membrane at an applied electric field 20V/cm, while at an intermediate field strength of 60 V/cm the smaller ovalbumin passed into the membrane, and at the high field strength of 100 V/cm the BSA is also driven into the membrane pores.
Figure 2C:
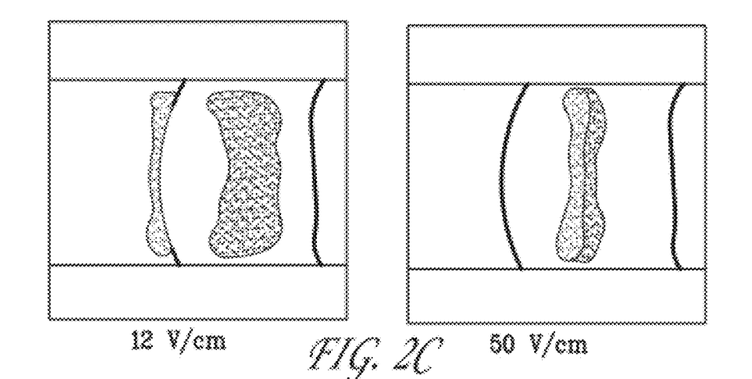
FIG. 2C shows the field selective gating of native vs. dye-labeled GFP, wherein dye-labeled GFP, imparted with higher negative charge, is driven into the zwitterionic methacrylate membrane at a lower applied electric field of 12 V/cm than unlabeled GFP while both are driven into the membrane at the high electric field of 50 V/cm.

Translocation of fluorescent proteins through gels was characterized by confocal microscopy as shown in FIGS. 2A-2C. Proteins were electrophoretically driven to the face of the gel membrane under the influence of an applied electric field, E, where they encountered nanopores limiting transport depending on protein conformation. Small molecules such as unconjugated fluorescent dyes readily passed through the pores while globular proteins larger than about 10 kDa were sterically excluded by native conformation larger than the pores. It was found that greater fields had to be applied for higher MW proteins to pass through the gel membrane pores. There was no measurable pore entry for proteins>27 kDa with E<10 Vcm$^{-1}$. At higher amplitude electric fields E, it is believed that electromechanical denaturation of proteins leads proteins that are unfolded into flexible pore-accessible conformations that allow for appreciable rates of translocation. This is qualitatively shown in FIGS. 2A and 2B which show a series of photomicrographs showing the field-dependence of protein exclusion. FIG. 2A shows fluorescently labeled BSA at 1, excluded in a narrow band from a zwitterionic membrane 2 with an applied electric field of E equal to 20 V/cm (left frame), but passing through membrane 2 at a higher applied field (right frames). The field threshold for exclusion was also protein specific as shown in FIG. 2B: at low voltages, both ovalbumin (3) and IgG (4) were excluded from an acrylamide membrane. However, at 50 V/cm, the ovalbumin (3) passed through the pores while IgG (4) remained excluded.

Additionally, there are different ways in which the structure and charge of proteins may be modified. In particular, the pH of the buffer/solvent environment within which individual proteins in solution may be modified. As the pH of the solution is decreased from a high extreme, the proteins become less net negatively charged, eventually reaching a net neutral isoelectric point. Below its isoelectric point the proteins in solution becomes more net positively charged. Furthermore, different proteins have different composition of titratable charge groups and wide-ranging isoelectric points. Our experiments have indicated that lowering the solution pH changes the exclusion threshold. Therefore, changing the pH of the analyte solution could help fractionate or characterize proteins based on differences in their titratable charge groups and resulting net charge. Moreover, we also showed that the exclusion threshold is altered by denaturing a protein with urea (in experiments with ovalbumin and BSA the exclusion thresholds were higher with urea).

In order to demonstrate size exclusion of the nanoporous membranes, various proteins were first tagged with a fluorescent dye and then loaded for a fixed period of time at a low field strength such that the proteins were enriched at the face of the exclusion membrane but excluded from migrating into its pores. Loading the proteins in this way took between 1-3 minutes at a field potential of 5-80 V/cm depending on the sample. The voltage drop across the short channel segment containing the exclusion membrane was measured with a high voltage probe built in-house with an internal resistance, $R_{in}$, equal to about $10^{11}$ ohms. For these experiments, the resistance of the exclusion membrane segments was found to be steady and comparable to the adjacent PAGE separation channels containing an 8% polyacrylamide sieving gel.

Following sample loading, a buffer solution indicated in FIG. 1C, was loaded from a separate reservoir (not shown) at a similar field strength so that no additional protein migration was introduced and that all proteins are confined near the exclusion membrane before raising the voltage. Moreover, the time-voltage product was held constant for the exclusion/transport tests such that higher fields were maintained for shorter times so that any protein loss at the exclusion membrane would be due to changes in size exclusion and not differences in electrophoretic mobility. During this period, some fraction of protein would enter the pores of the exclusion membrane depending on the field strength and size/charge/structure of each of the proteins. All proteins were focused at the exclusion membrane face.

Analysis of the fraction of proteins remaining at the surface of the exclusion membrane was performed by applying a much higher reverse field across the exclusion membrane and through the adjacent separation channel where the fraction of protein excluded from the membrane was quantified by laser induced fluorescence of separated protein bands. Changes in protein exclusion at different field strengths were also characterized directly at the exclusion membrane by fluorescence microscopy of excluded and membrane permeated protein fractions. It is noted that since unconjugated dye to molecules were small enough to freely pass through the exclusion membrane, these species were no longer present after loading the buffer solution.

This procedure was repeated several times at successively higher sample loading field potentials. Furthermore, the duration of each of the sample loading steps was decreased such that the time-voltage product was held constant as mentioned above. After each sample is loading step was completed an electropherogram of the proteins remaining at the face of the exclusion membrane was performed by PAGE separation analysis. Each of the peaks of the individual electropherograms was then measured and normalized against the measure peaks of an electropherogram of the same group of proteins prior to sample loading.

Examples

The fractionation of specific proteins was demonstrated quantitatively using aqueous mixtures of up to 4 proteins ranging in size from 27 kDa to 150 kDa. Green fluorescent protein (GFP) at 27 kDa, fluorescently tagged Annexin V protein (AnV) at 36 kDa, fluorescently tagged ovalbumin (OVA) at 45 kDa, fluorescently tagged bovine serum albumin (BSA) at 67 kDa, fluorescently tagged transferrin (TF) at 85 kDa, and fluorescently tagged immunoglobulin G protein (IgG) at 150 kDa were all concentrated at membrane 1, shown in FIG. 2A, with an applied electric field from between 5 V/cm to greater than 300 V/cm.

Figure 3A:
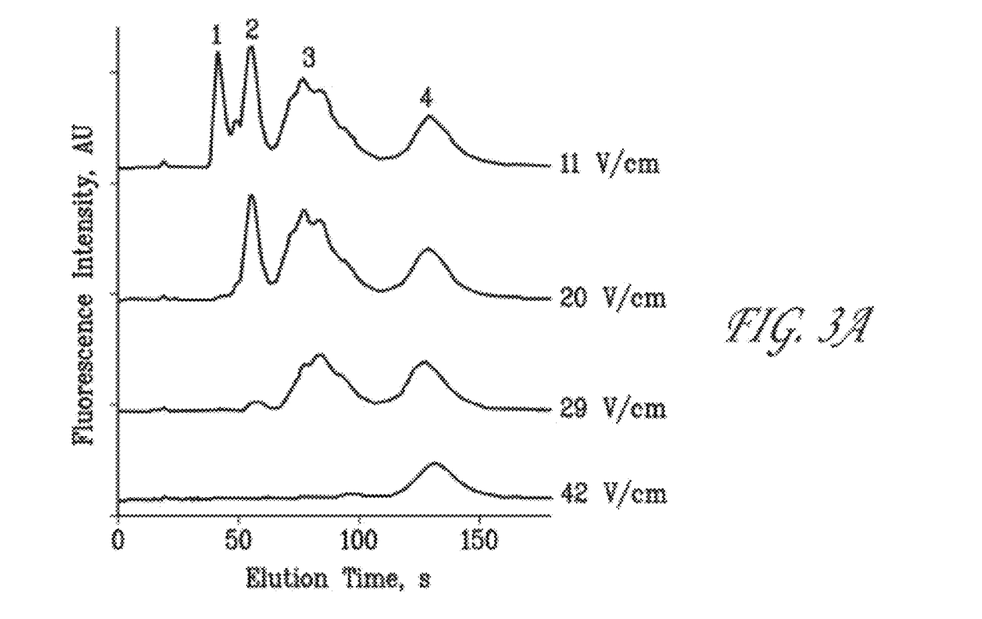
FIG. 3A shows electropherograms of excluded proteins in a mixture of four proteins quantified by integrated PAGE separation analysis, where peaks 1-4 correspond to GFP, OVA, TF and IgG, respectively. At E=11 V/cm, all 4 proteins are gated, while individual proteins are stepwise removed from the mixture, based on size, as the electric field is increased incrementally.

In the present case, the sample loading potential was begun at about 7 volts/cm and increased incrementally. Mixtures of up to 4 proteins were evaluated simultaneously. Field thresholds were sharp and specific enough that proteins were removed piecewise from a mixture by simply adjusting the applied voltage. Examples of the electropherograms obtained by the fractionation process are shown in FIG. 3A (Peaks 1-4 correspond respectively to GFP, OVA, TF and IgG). The electropherograms were established by PAGE separation analysis of the remaining fraction of proteins at the exclusion membrane after sample loading at several successively higher loading potentials.

The relatively sharp and distinct field thresholds for the proteins investigated here were exploited to piecewise remove proteins from a mixture by adjusting electric field potential. As shown in FIG. 3A, at low E across the exclusion membrane (~11 V/cm), all 4 of the proteins in the mixture were initially blocked by the size exclusion membrane. However, at increasing field strengths, it was possible to selectively gate 1, 2, or 3 of the 4 proteins while the other(s) passed through the exclusion membrane pores. The field-threshold of translocation correlated roughly with protein chain-length as shown in FIG. 3C.

Figure 3B:
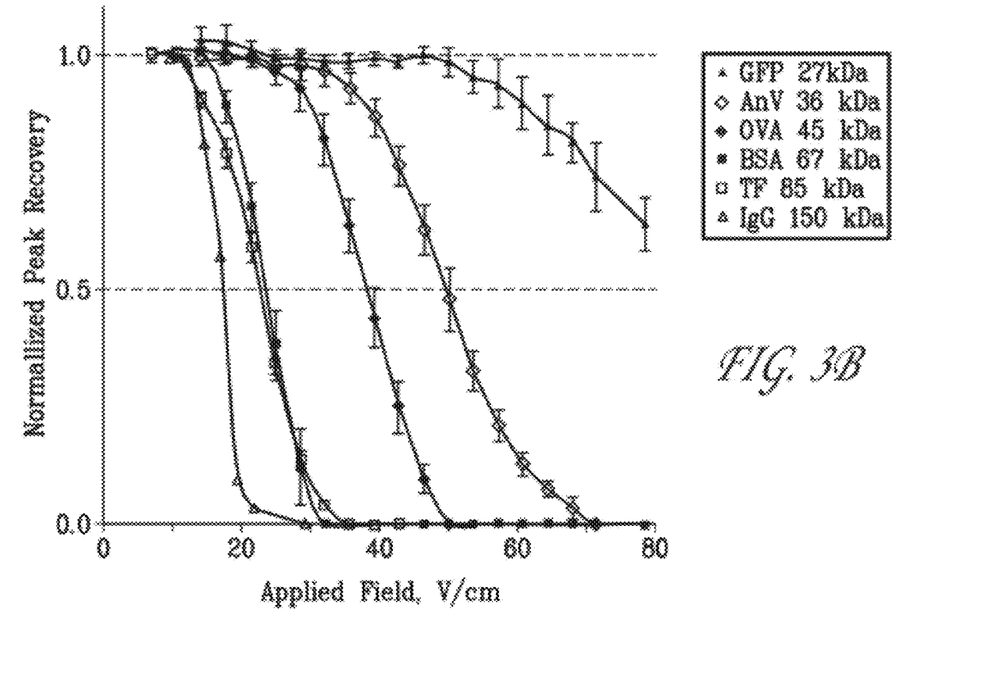
FIG. 3B graphically illustrates protein size exclusion as a function of the applied electric field, E.
Figure 3C:
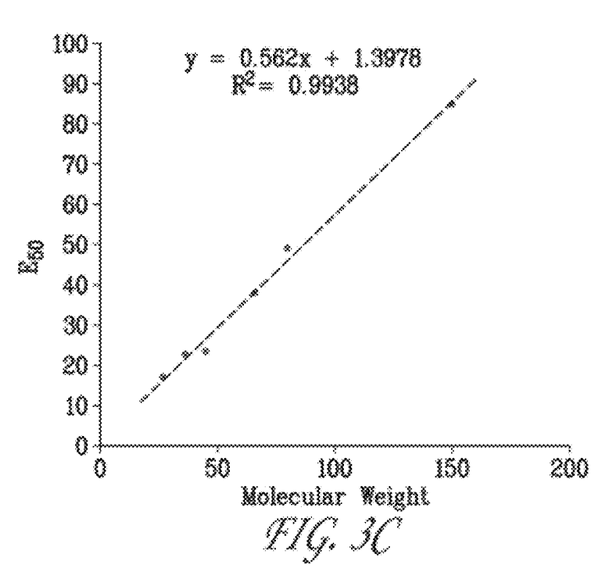

After repeating these steps multiple times and thereby generating the individual curves shown in FIG. 3B, the field potential corresponding to the 50% normalized peak recovery point ($E_{50}$) for each curve was measured. The value of $E_{50}$ was then plotted as a function of protein molecular weight as is shown in FIG. 3C and summarized in Table 1 below.

TABLE 1

| Protein | MW (kDa) | E50 (V/cm) |
|---|---|---|
| GFP | 27 | 16.9 |
| AnV | 36 | 22.5 |
| OVA | 45 | 23.6 |
| BSA | 67 | 38.5 |
| TF | 85 | 49.3 |
| IgG | 150 | 84.6 |

Figure 4A:
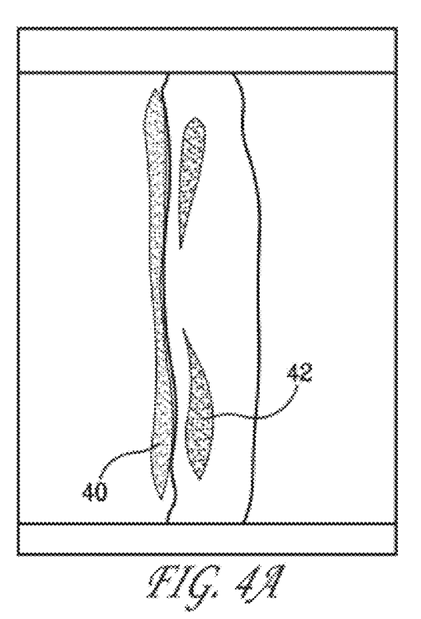
FIG. 4A shows the field selective gating of ALEXA-FLUOR® 488 labeled allophycocyanin (APC), wherein non-crosslinked APC is driven into the membrane at a field strength of 80 V/cm.
Figure 4B:
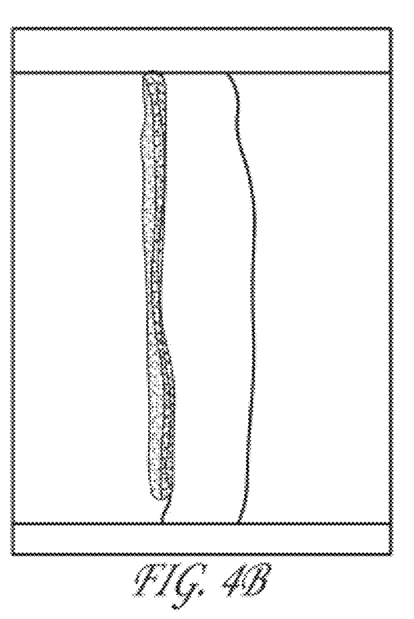
FIG. 4B shows the field selective gating of ALEXA-FLUOR® 488 labeled APC, wherein crosslinked APC is gated at a field strength of 80 V/cm.

To further test the basis of field-dependent size exclusion, rigid molecules with dimensions similar to folded proteins were tested. Rigid 6.2 nm diameter quantum dots were concentrated at the exclusion membrane, but were excluded at fields up to 1,000 V/cm, supporting the hypothesis that proteins must unfold to pass through the pores. Natively fluorescent proteins were also tested for a reduction in fluorescence that might be expected by field-driven denaturing. In particular, hexameric protein allophycocyanin (APC) shows a dramatic loss of native fluorescence, on the order of >80%, associated with APC translocation, presumably due to APC denaturing and most likely dissociating into subunits. Therefore, the exclusion of APC was also compared to that of cross-linked APC (APC-XL). Unfolding and dissociation of the subunits is prevented by cross-links that stabilize the folded state of APC-XL. As would be expected, for a protein unfolding mechanism of translocation, APC-XL had a higher exclusion threshold. Tests of ALEXA FLUOR® 488 labeled versions of APC and APC-XL highlight differences between APC and APC-XL exclusion. FIG. 4A shows non-crosslinked APC 42 is driven into the membrane at 80 V/cm while FIG. 4B shows that crosslinked APC (i.e., APC-XL) is gated at this field strength. A >80% loss of native APC fluorescence 40 is associated with denaturation of APC compared to negligible change in fluorescence of conjugated dye 42 during translocation. The denaturation of APC with 8 M urea or with high pressure at 0° C. has been shown to similarly reduce native APC fluorescence (see Foguel, et al., *Journal of Biological Chemistry*, 1995, v. 270: pp. 28759).

An ALEXA FLUOR® 647-labeled version of GFP was also tested. In contrast to the $\geq$15% drop in native GFP fluorescence, no appreciable drop was observed for the dye-labeled fluorescence. There was, however, a difference in the exclusion properties of dye-labeled and native GFP as shown in FIG. 2C. The dye-labeled GFP had a slightly lower exclusion threshold which is attributed to greater negative charge for the labeled protein (possibly destabilized by the presence of the dye). By choosing a field in between the exclusion-thresholds of GFP and labeled-GFP, it was possible to fractionate the sample.

Figure 5A:
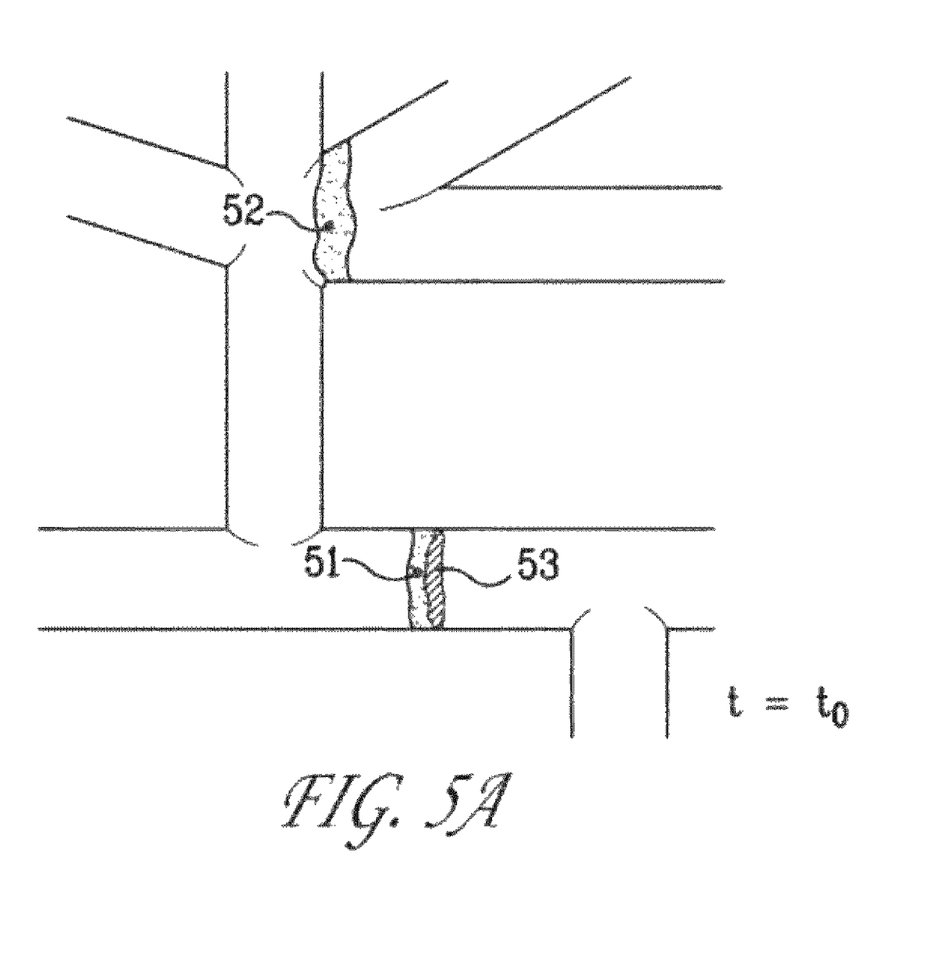
FIG. 5A shows a magnified view of a field selective membrane network wherein green fluorescent protein (GFP) is excluded at first membrane, $M_1$, with $E_1 < E_{50}$.
Figure 5B:
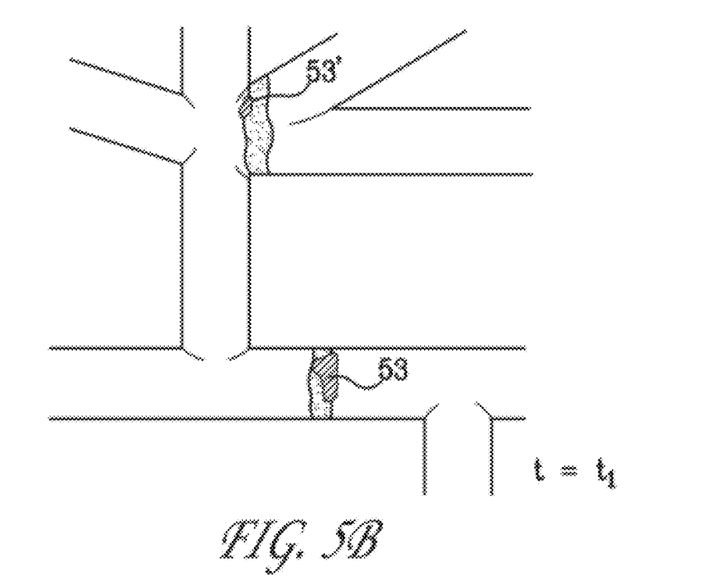
FIGS. 5B and 5C show the magnified view of a field selective membrane network of FIG. 5A wherein $E_1$ is raised $> E_{50}$ at first membrane 51 but $E_2 < E_{50}$; GFP passes through membrane 51 and is trapped at second membrane 52.
Figure 5C:
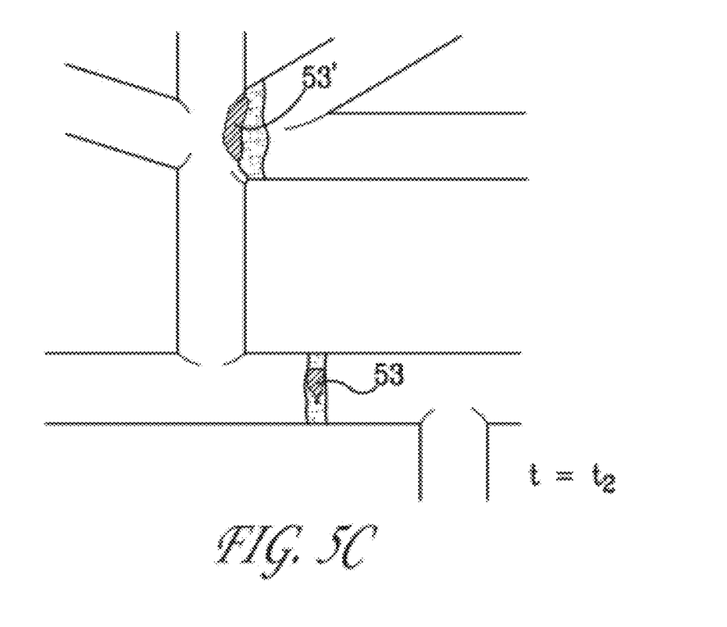
Figure 6:
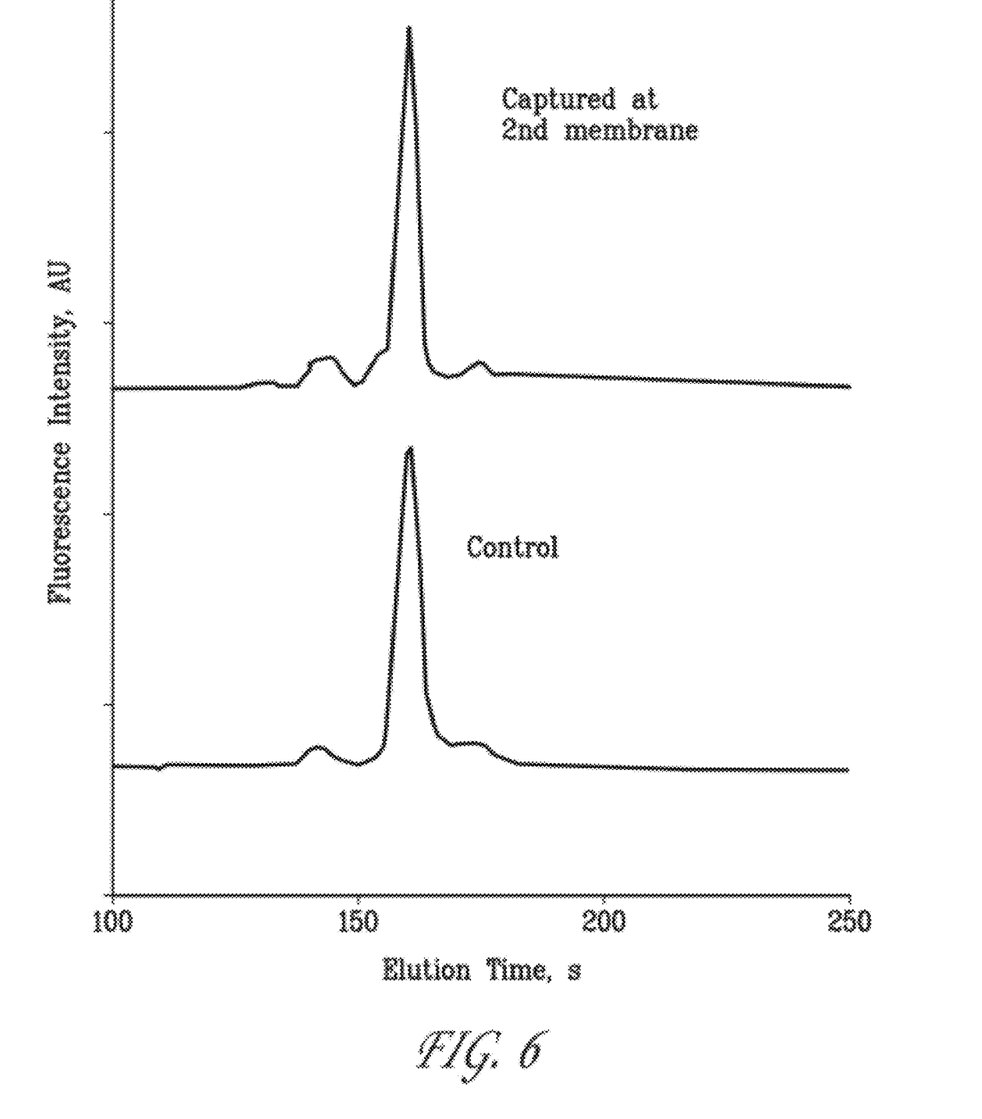
FIG. 6 illustrates an integrated PAGE analysis of GFP recaptured at second membrane 52 of FIG. 5C showing that the native structure of the GFP molecule has been restored.

Lastly, integrating a system of exclusion membranes gives additional flexibility for continuous fractionating and preconcentration of proteins in a dense network. To demonstrate this, we fabricated a simple serial array of two exclusion membranes, 51 and 52 to evaluate refolding and capture of protein at a second membrane. This structure is shown in FIG. 5A, wherein GFP 53 is shown excluded from membrane 51 at time $t_0$ when electrical field $E_1$ is set below a certain threshold. However, as shown in FIGS. 5B and 5C, when field $E_1$ is set above the threshold at first exclusion membrane 51 but below the threshold at second exclusion membrane 52, GFP 53 begins to migrate through membrane 51 and toward membrane 52 where it is trapped at membrane 52 (53' at $t=t_1$). If the electric field is maintained at or below this level for a period of time, as is shown in FIG. 5C, GFP 53 continues to migrate through membrane 51 and continues to be concentrated at the membrane 52 (53' at $t=t_2$). The GFP was confirmed to be unaffected by passage through membrane 51: there was no detectable difference in conformation as determined by fluorescence and integrated PAGE analysis of the recaptured GFP as shown in FIG. 6. This demonstrates the ease to which integrated analysis features could be coupled with each exclusion membrane in a network comprising either a serial or parallel arrangement of membranes, or combinations therefore.

Other more complex combinations are also possible. If several of the nanoporous membranes are placed in series, a useful embodiment would comprise having a desired fraction of the sample of proteins pass through a first membrane, either under the influence of a high electric field and/or due to larger membrane pores, and then having further fractions pass through or become trapped at successive membranes. This embodiment would require incrementally decreasing the electric field and/or decreasing the membrane pore sizes.

An alternative embodiment would comprise several nanoporous membranes placed in parallel, wherein the protein sample is delivered to a first membrane, and whatever quantity of protein that is not driven through the first membrane by a first electric field, is subsequently delivered to a second membrane. However, in this embodiment, the first membrane would comprise the lowest electric field and/or smallest pores and each successive membrane in parallel would comprise an incrementally increasing electric field and/or larger pores.

It is therefore demonstrated that proteins may be effectively fractionated using the methods and materials described herein. Applications include step-wise voltage-tunable fractionation of a complex protein mixture in a simple chip with just one exclusion membrane. Moreover, the present approach may provide the ability to characterize protein conformation, folding and stability based on field-dependent transport through nanoporous exclusion membranes.

Having thus described exemplary embodiments of the present invention, it should be noted by those skilled in the art that the disclosures herein are exemplary only and that various other alternatives, adaptations, and modifications may be made within the scope of the present invention. Accordingly, the present invention is not limited to the specific embodiments as illustrated herein, but is only limited by the following claims.

Finally, to the extent necessary to understand or complete the disclosure of the present invention, all publications, patents, and patent applications mentioned herein are expressly incorporated by reference therein to the same extent as though each were individually so incorporated.

What is claimed is:

1. A method, comprising the steps of:
(i) providing a fractionation channel comprising a nanoporous membrane about 15 µm to 100 µm in length fixedly attached therein, and an analyte reservoir and a waste reservoir in fluid communication with the fractionation channel, wherein the nanoporous membrane further comprises a cross-linked polymer having a plurality of pores having an average diameter of about 2 nm;
(ii) introducing an analyte solution into the analyte reservoir, wherein the analyte solution comprises a plurality of proteins comprising native conformations larger in size than the average diameter of the plurality of pores;
(iii) applying a first electric field having a polarity directed toward a first face of the nanoporous membrane, wherein the first electric field electrophoretically transports a quantity of the plurality of proteins to the first face, and wherein the plurality of proteins is initially excluded from entering the nanoporous membrane;
(iv) increasing the first applied electric field by a predetermined incremental voltage and maintaining the increased applied electric field for a fixed period of time;
(v) repeating step (iv) while increasing the applied electric field by the predetermined incremental voltage with each step until a first fraction of the plurality of proteins is transported a distance into or through the nanoporous membrane;
(vi) performing a PAGE separation analysis of remaining protein fractions disposed at the first face;
(vii) repeating step (iv) while increasing the applied electric field by the predetermined incremental voltage with each step until an additional fraction of the plurality of proteins is transported a distance into or through the nanoporous membrane or until a predetermined maximum electric field is reached or surpassed; and
(viii) repeating step (vi) after each additional fraction of proteins has been transported into or through the nanoporous membrane.

2. The method of claim 1, wherein the plurality of proteins comprise one or more groups of proteins.

3. The method of claim 2, wherein each group of proteins comprises a different physical parameter selected from the group of parameters consisting of molecular size, electric charge, and molecular conformation.

4. The method of claim 3, wherein the pH of the analyte solution is adjusted by an increment that changes one or more of the physical parameters of the one or more group of proteins.

5. The method of claim 3, wherein the solvent is adjusted by an increment that changes one or more of the physical parameters of the one or more group of proteins.

6. The method of claim 1, further comprising one or more buffer solution and one or more processing channels each in fluid communication with the fractionation channel.

7. The method of claim 6, wherein the step of introducing the analyte solution further comprises introducing an analyte solution and a buffer solution into the fractionation channel.

8. The method of claim 7, wherein the step of electrophoretically transporting further comprises the step of electrophoretically transporting a quantity of the analyte solution under the first applied electric field toward the first face, thereby concentrating the quantity of proteins at the first face.

9. The method of claim 1, wherein the step of repeating step (iv) further comprises decreasing the period of time during which each incremented electric field is maintained such that the time-voltage product is maintained about constant.

10. The method of claim 1, wherein the cross-linked polymer is a polymethacrylate.

11. The method of claim 1, wherein the cross-linked polymer is a polyacrylamide gel.

12. The method of claim 1, wherein the first applied electric field is about 5 Volts/cm.

13. The method of claim 1, wherein the quantity of the plurality of proteins passing through the nanoporous membrane is measured during step (iv).

14. The method of claim 13, wherein quantity of protein passing through the nanoporous membrane during step (iv) is measured by fluorescence detection.

15. The method of claim 13, wherein quantity of protein passing through the nanoporous membrane during step (iv) is measured by changes in electrical conductance or impedance of the nanoporous membrane.

16. A method, comprising the steps of:
(i) providing a fractionation channel comprising n nanoporous membranes, where n is an integer, fixedly attached therein in series, and one or more analyte reservoirs and one or more waste reservoirs in fluid communication with the fractionation channel, wherein each of the n nanoporous membranes is about 15 µm to 100 µm in length and further comprises a cross-linked polymer having a plurality of pores having an average diameter of about 2 nm;
(ii) introducing an analyte solution into the one or more analyte reservoirs, wherein the analyte solution comprises a plurality of proteins comprising native conformations larger in size than the average diameter of the plurality of pores;
(iii) applying a first electric field across a first face of a first of the n nanoporous membranes, wherein the first electric field has a polarity directed toward the first face of the first nanoporous membrane thereby electrophoretically transporting a quantity of the plurality of proteins to the first face, and wherein the plurality of proteins are initially excluded from entering the first of the nanoporous membranes in the series of n nanoporous membranes;
(iv) increasing and maintaining the first applied electric field at a predetermined maximum voltage thereby electrophoretically transporting some or all of the quantity of proteins through the first nanoporous membrane;
(v) setting and maintaining a next electric field incrementally less than the electric field across the immediately preceding nanoporous membrane across a first face of a next one of the n nanoporous membranes, wherein the next electric field has a polarity directed toward the first face of the next one of the n nanoporous membranes in series, and some or all of the proteins passing through the preceding nanoporous membrane are electrophoretically transporting though the next successive one of the n nanoporous membranes; and
(vi) repeating step (v) n−2 times or until no additional quantity of proteins pass through a last nanoporous membrane.

17. The method of claim 16, wherein each of the n nanoporous membranes comprise an average pore size which successively decreases from the first nanoporous membrane to the $n^{th}$ nanoporous membrane.

18. The method of claim 16, wherein the cross-linked polymer is a polymethacrylate.

19. The method of claim 16, wherein the cross-linked polymer is a polyacrylamide gel.

20. A method, comprising the steps of:
(i) providing a plurality of n fractionation channels, where n is a first integer, each comprising a nanoporous membrane about 15 μm to 100 μm in length and further comprising a cross-linked polymer having a plurality of pores having a first average diameter, fixedly attached therein, wherein the n fractionation channels are arranged in parallel, and wherein each fractionation channel is in fluid communication with an analyte reservoir, a waste reservoir, and with each of the other n fractionation channels;
(ii) introducing an analyte solution comprising a plurality of proteins into the one or more of the analyte reservoirs comprising native conformations larger in size than the first average diameter of the plurality of pores;
(iii) applying a first electric field having a first voltage potential and a polarity directed toward a first face of the nanoporous membrane of an $i^{th}$ fractionation channel, where i is a second integer increasing from 1 to n, thereby electrophoretically transporting a quantity of the plurality of proteins toward the first face of the nanoporous membrane disposed in the $i^{th}$ fractionation channel, and wherein the plurality of proteins are initially excluded from entering the nanoporous membranes disposed therein;
(iv) increasing the first voltage potential by an $i^{th}$ predetermined increment to provide an $i^{th}$ electric field having an $i^{th}$ voltage potential and maintaining the $i^{th}$ electric field for a period of time thereby driving a portion of the plurality of proteins into and/or through the nanoporous membrane of the $i^{th}$ fractionation channel;
(v) removing the $i^{th}$ electric field;
(vi) applying an $i^{th}+1$ electric field having an $i^{th}+1$ voltage potential equal to the $i^{th}$ voltage potential and a polarity directed away from the $i^{th}$ fractionation channel and toward a first face of a nanoporous membrane of an $i^{th}+1$ fractionation channel, thereby electrophoretically transporting a remaining portion of the plurality of proteins toward the first face of the nanoporous membrane of the $i^{th}+1$ fractionation channel;
(vii) increasing the $i^{th}+1$ voltage potential by an $i^{th}+1$ predetermined increment greater than the $i^{th}$ predetermined increment and maintaining the $i^{th}+1$ voltage potential for a period of time thereby driving a next portion of the remaining portion of the plurality of proteins into and/or through the nanoporous membrane of the $i^{th}+1$ fractionation channel; and
(viii) increasing i by 1 and repeating steps (iii) and (vii) until the $i^{th}+1$ fractionation channel is equal to the $n^{th}$ fractionation channel.

21. The method of claim 20, wherein each of the n nanoporous membranes comprise an average pore size which successively decrease from the first nanoporous membrane to the $n^{th}$ nanoporous membrane.

22. The method of claim 20, wherein the cross-linked polymer is a polymethacrylate.

23. The method of claim 20, wherein the cross-linked polymer is a polyacrylamide gel.

* * * * *